(12) United States Patent
Yamakita

(10) Patent No.: US 7,715,524 B2
(45) Date of Patent: May 11, 2010

(54) RADIATION IMAGE CAPTURING APPARATUS

(75) Inventor: Hiroshi Yamakita, Minami-ashigara (JP)

(73) Assignee: FUJIFILM Corporation, Tokyo (JP)

( * ) Notice: Subject to any disclaimer, the term of this patent is extended or adjusted under 35 U.S.C. 154(b) by 26 days.

(21) Appl. No.: 12/057,993

(22) Filed: Mar. 28, 2008

(65) Prior Publication Data

US 2009/0041183 A1 Feb. 12, 2009

(30) Foreign Application Priority Data

Mar. 28, 2007 (JP) .............................. 2007-083226

(51) Int. Cl.
*A61B 6/04* (2006.01)
*G21K 1/00* (2006.01)

(52) U.S. Cl. .................. 378/37; 378/154; 378/155; 378/196; 378/197

(58) Field of Classification Search .................. 378/37, 378/154, 155, 196, 197
See application file for complete search history.

(56) References Cited

U.S. PATENT DOCUMENTS

| | | | | |
|---|---|---|---|---|
| 4,969,174 A | * | 11/1990 | Scheid et al. | 378/146 |
| 4,970,398 A | * | 11/1990 | Scheid | 250/374 |
| 4,998,270 A | * | 3/1991 | Scheid et al. | 378/155 |
| 5,040,202 A | * | 8/1991 | Scheid | 378/155 |
| 5,212,719 A | * | 5/1993 | Virta et al. | 378/155 |
| 5,872,828 A | * | 2/1999 | Niklason et al. | 378/23 |
| 6,088,427 A | * | 7/2000 | Pagano | 378/155 |
| 6,438,210 B1 | * | 8/2002 | Castleberry | 378/154 |
| 6,470,072 B1 | * | 10/2002 | Johnson | 378/154 |
| 6,882,700 B2 | * | 4/2005 | Wang et al. | 378/37 |
| 6,999,554 B2 | * | 2/2006 | Mertelmeier | 378/37 |
| 7,123,684 B2 | * | 10/2006 | Jing et al. | 378/37 |
| 7,319,735 B2 | * | 1/2008 | Defreitas et al. | 378/37 |
| 7,327,826 B2 | * | 2/2008 | Hanke et al. | 378/37 |
| 7,443,949 B2 | * | 10/2008 | Defreitas et al. | 378/37 |
| 7,443,950 B2 | * | 10/2008 | Sendai | 378/37 |
| 7,566,172 B2 | * | 7/2009 | Kashiwagi | 378/205 |

FOREIGN PATENT DOCUMENTS

JP 2005-013344 A 1/2005

* cited by examiner

*Primary Examiner*—Allen C. Ho
(74) *Attorney, Agent, or Firm*—Sughrue Mion, PLLC

(57) ABSTRACT

A grid comprises an alternate assembly of radiation-permeable members and radiation-impermeable members which extend substantially parallel to the chest wall of a subject. When a radiation emitted from a radiation source is applied through a breast of the subject and the grid to a radiation detector, a radiation image of the breast is captured. While the radiation is being applied to the breast, the grid reciprocates in directions perpendicular to the direction in which the radiation-impermeable members extend.

13 Claims, 8 Drawing Sheets

PRIOR ART

PRIOR ART

RADIATION IMAGE CAPTURING APPARATUS

BACKGROUND OF THE INVENTION

1. Field of the Invention

The present invention relates to a radiation image capturing apparatus for capturing a radiation image of a subject by applying a radiation emitted from a radiation source to the subject and detecting the radiation that has passed through the subject with a radiation detector.

2. Description of the Related Art

In the medical field, there have widely been used radiation image capturing apparatus, known as mammographic apparatus, which apply a radiation emitted from a radiation source to a breast of a subject and detect the radiation that has passed through the breast with a radiation detector.

One known radiation detector for use in the radiation image capturing apparatus includes a solid-state detector in a laminated structure comprising a matrix of charge collecting electrodes formed on an insulating substrate and a radiation conductor disposed on the charge collecting electrodes for generating electric charges depending on the radiation that is applied. The electric charges generated by the radiation conductor and representing radiation image information are collected by the charge collecting electrodes and temporarily stored in an electric storage unit. The collected electric charges are converted into an electric signal, which is output from the solid-state detector. Other known radiation detectors include a radiation detector comprising a charge-coupled device (CCD) and a radiation detector comprising a combination of amorphous silicon and a scintillator. Furthermore, a stimulable phosphor panel which, when exposed to an applied radiation (X-rays, $\alpha$-rays, $\beta$-rays, $\gamma$-rays, electron beams, ultraviolet radiation, or the like), stores part of the energy of the radiation, and, when subsequently exposed to applied stimulating light such as laser beam, visible light, or the like, emits stimulated light in proportion to the stored energy of the radiation, may also be used as a radiation detector.

In order to obtain a high-quality radiation image captured by a radiation detector, as shown in FIGS. 7 and 8 of the accompanying drawings, a grid 6 is disposed in front of a radiation detector 2 for preventing scattered rays of a radiation X that are generated in a subject 4 from entering the radiation detector 2, as disclosed in Japanese laid-open patent publication No. 2005-13344. As well known in the art, the grid 6 is a convergent grid comprising an alternate assembly of radiation-permeable members 8 made of aluminum or the like which pass the radiation X therethrough and radiation-impermeable members 10 made of a material including lead or the like, the radiation-impermeable members 10 being inclined parallel to the direction in which the radiation X is applied to the grid 6.

On the mammographic apparatus, it is customary to capture various radiation images of the breast in different directions, e.g., vertically, horizontally, and obliquely. Depending on the size of the breast, the breast may not be properly positioned in a prescribed position on the radiation detector 2. If the breast is not properly positioned in the desired position on the radiation detector 2, then the position of the radiation source 12 is changed into alignment with the position of the breast for appropriately irradiating the breast with the radiation X.

When the position of the radiation source 12 is changed, however, since the direction in which the radiation X is applied and the direction in which the radiation-impermeable members 10 of the grid 6 are inclined are brought out of alignment with each other, part of the radiation X may possibly be vignetted by the radiation-impermeable members 10.

In recent years, efforts have been made to perform tomosynthesis and stereoscopic imaging using mammographic apparatus. According to these imaging processes, the radiation source 12 is turned around the breast 4 in the directions indicated by the arrow $\alpha$ as shown in FIG. 7 to acquire a three-dimensional image or a desired sectional image of the breast 4. As the radiation source 12 is turned around the breast 4, the radiation X emitted from the radiation source 12 falls upon the grid 6 in constantly changing directions. Therefore, the radiation X is partly vignetted by the radiation-impermeable members 10 during the imaging process.

In order to avoid the vignetting, the grid 6 may be turned in the directions indicated by the arrows $\beta$ as shown in FIG. 7 in synchronism with the turning of the radiation source 12. Consequently, an additional mechanism is required to move the grid 6, and also an additional space for moving the grid 6 therein is required to allow the grid 6 to be turned in synchronism with the turning of the radiation source 12. Another problem is that the quality of the generated image of the breast 4 tends to be lowered because the positional relationship between the grid 6 and the radiation detector 2 varies as the grid 6 moves.

SUMMARY OF THE INVENTION

It is a general object of the present invention to provide a radiation image capturing apparatus which is of a highly simple structure capable of capturing a high-quality radiation image by avoiding an image quality degradation due to the movement of a radiation source with respect to a subject.

A major object of the present invention is to provide a radiation image capturing apparatus which is capable of capturing a high-quality radiation image by moving a radiation source only without the need for moving a grid.

Another object of the present invention is to provide a radiation image capturing apparatus which is capable of capturing a high-quality radiation image free of shadows of a grid when the grid is movable.

Still another object of the present invention is to provide a radiation image capturing apparatus which is capable of capturing a high-quality radiation image when the radiation image capturing apparatus is applied to tomosynthesis and stereoscopic imaging.

The above and other objects, features, and advantages of the present invention will become more apparent from the following description when taken in conjunction with the accompanying drawings in which preferred embodiments of the present invention are shown by way of illustrative example.

DESCRIPTION OF THE PREFERRED EMBODIMENTS

Figure 1:
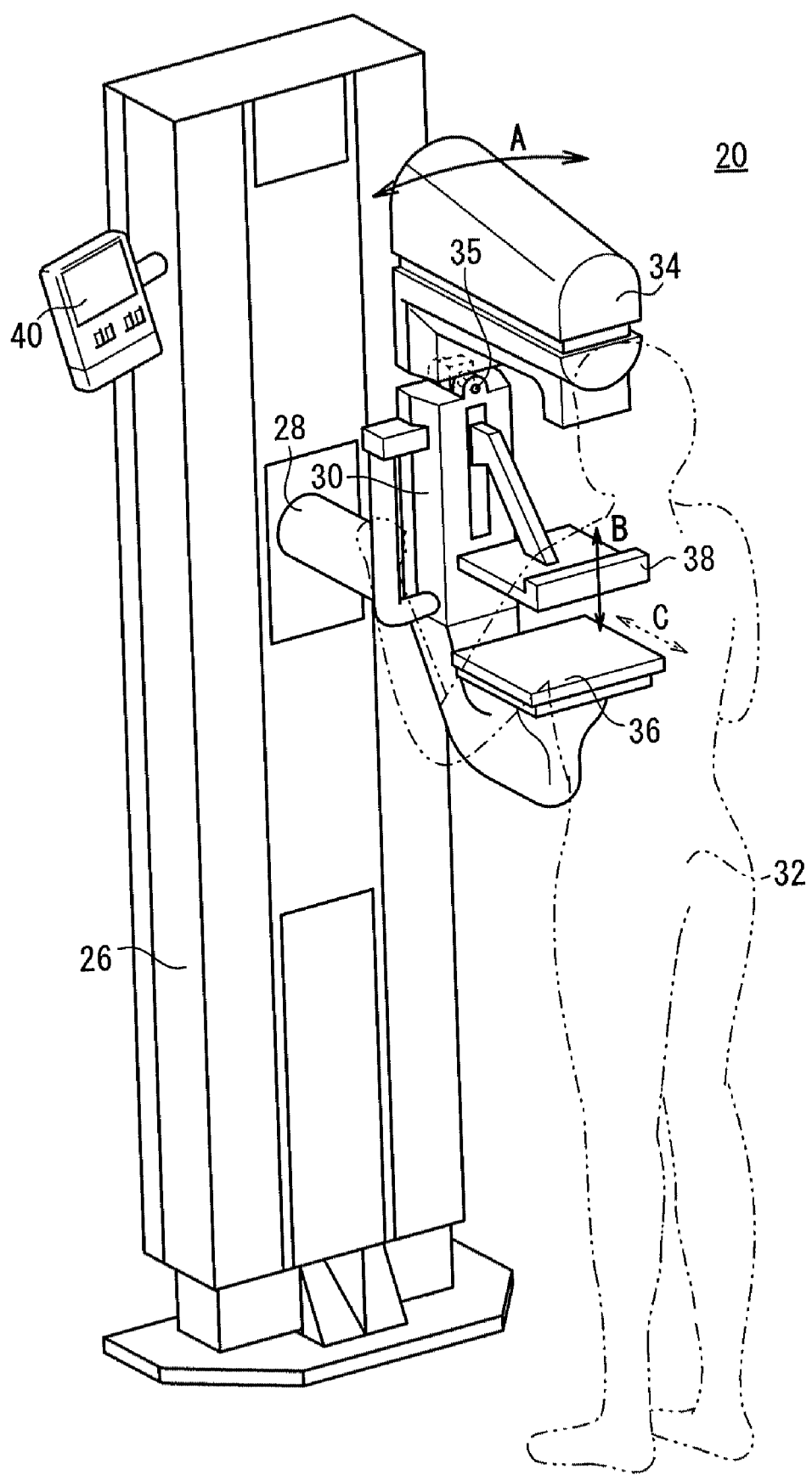
FIG. 1 is a perspective view of a mammographic apparatus according to an embodiment of the present invention.

FIG. 1 shows in perspective a mammographic system 20 according to an embodiment of the present invention, to which a radiation image capturing apparatus according to the present invention is applied.

As shown in FIG. 1, the mammographic system 20 includes an upstanding base 26, a vertical arm 30 fixed to a horizontal swing shaft 28 disposed substantially centrally on the base 26, a radiation source housing unit 34 storing a radiation source 22 (see FIG. 3) for applying a radiation X to a breast 44 (see FIG. 2) to be imaged of a subject 32 and fixed to an upper end of the arm 30, an image capturing base 36 housing a solid-state detector (radiation detector) 24 (see FIGS. 2 and 3) for detecting a radiation X that has passed through the breast 44 and a grid 23 and fixed to a lower end of the arm 30, and a compression plate 38 for compressing and holding the breast 44 against the image capturing base 36.

When the arm 30, to which the radiation source housing unit 34 and the image capturing base 36 are secured, is angularly moved about the swing shaft 28 in the directions indicated by the arrow A, an image capturing direction with respect to the breast 44 of the subject 32 is adjusted. The radiation source housing unit 34 is coupled to the arm 30 by a hinge 35 and is angularly movable in the directions indicated by the arrow A independently of the image capturing base 36. The compression plate 38 that is coupled to the arm 30 is disposed between the radiation source housing unit 34 and the image capturing base 36. The compression plate 38 is vertically displaceable along the arm 30 in the directions indicated by the arrow B.

To the base 26, there is connected a display control panel 40 for displaying image capturing information including an image capturing region, an image capturing direction, etc. of the subject 32, the ID information of the subject 32, etc., and setting these items of information, if necessary.

Figure 2:
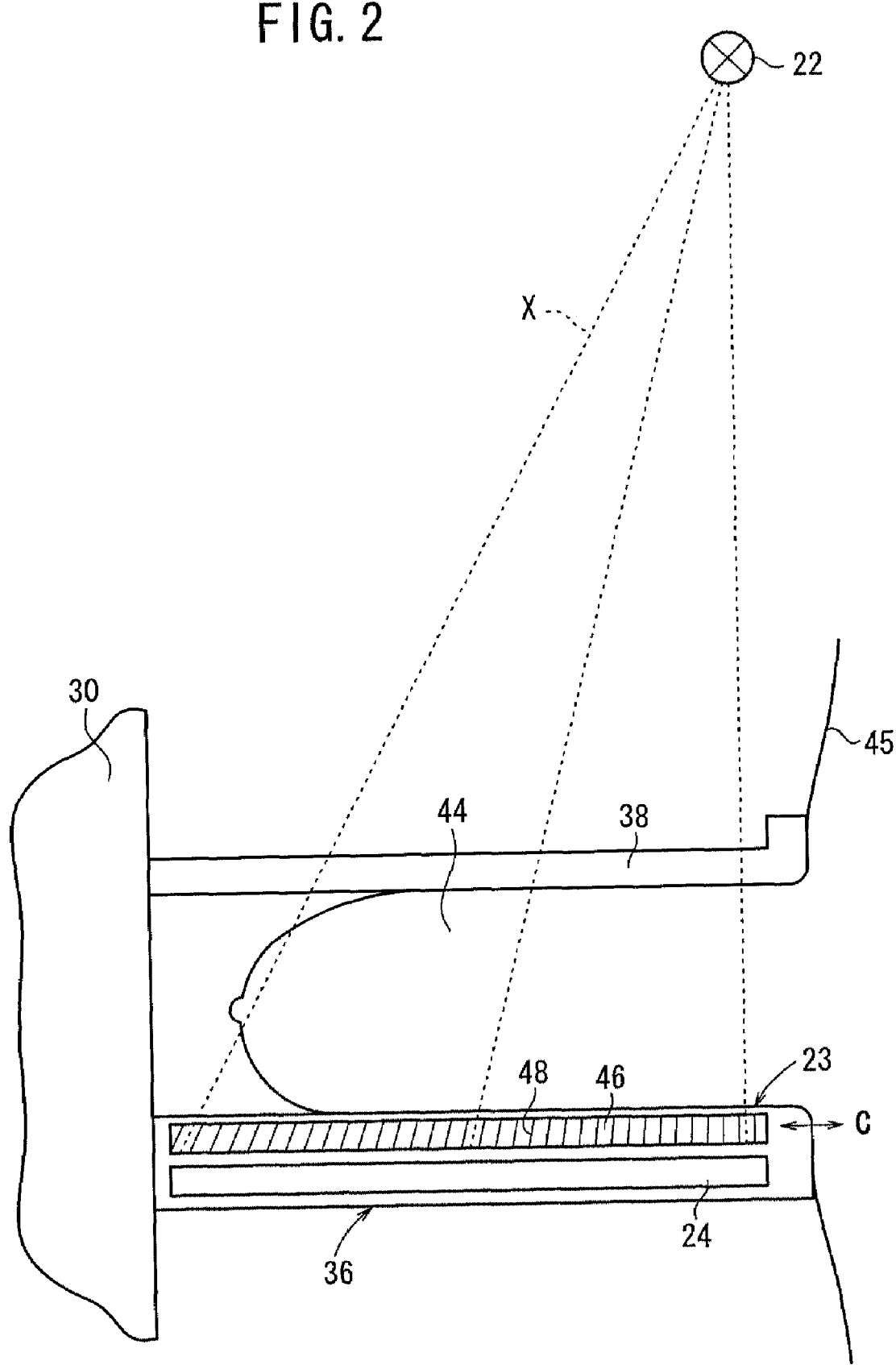
FIG. 2 is a fragmentary vertical elevational view, partly in cross section, showing internal structural details of an image capturing base of the mammographic apparatus according to the embodiment of the present invention.
Figure 3:
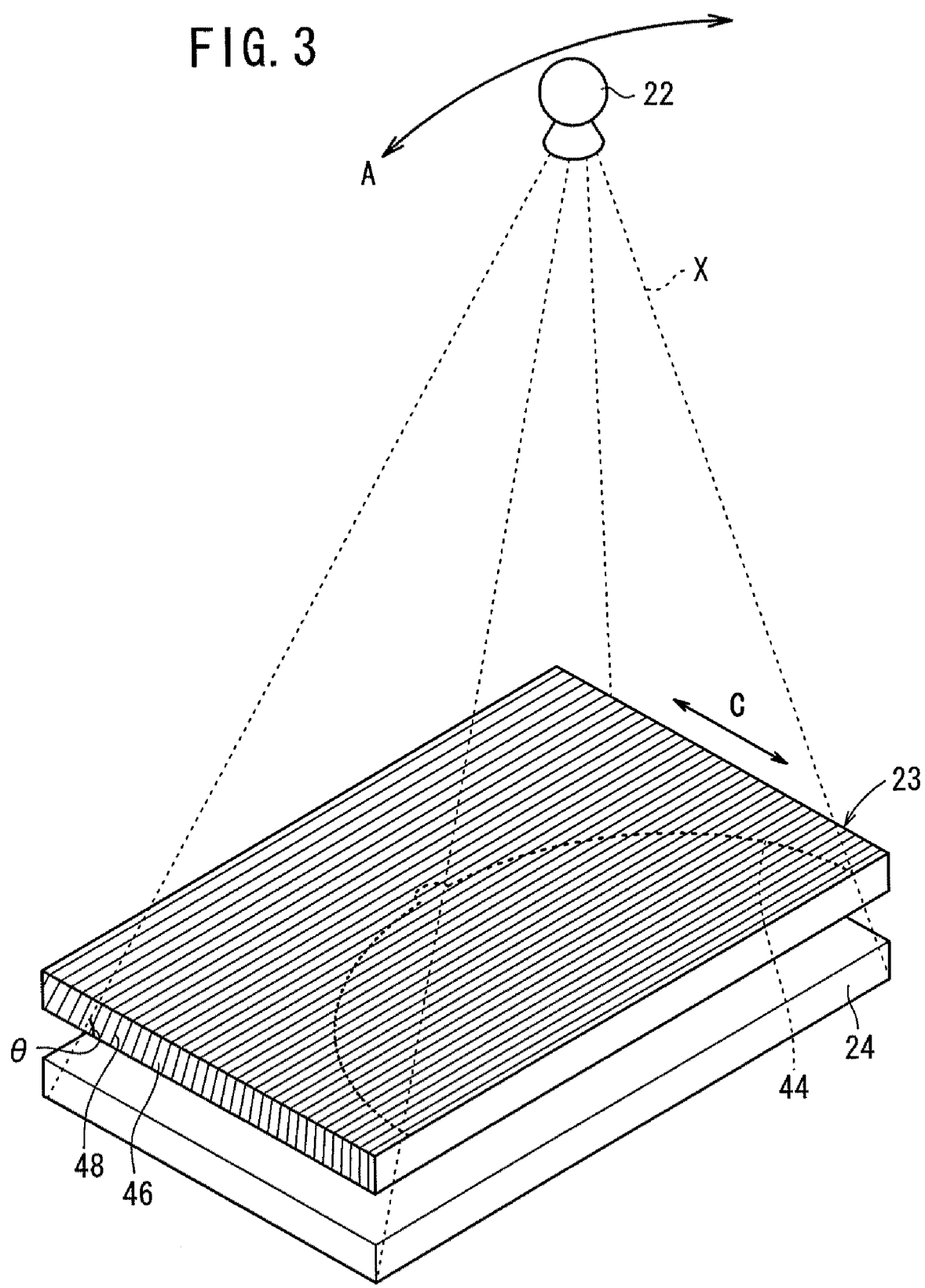
FIG. 3 is a perspective view of a grid of the mammographic apparatus according to the embodiment of the present invention.

FIGS. 2 and 3 show internal structural details of the image capturing base 36 of the mammographic system 20. In FIG. 2, the breast 44 of the subject 32 is shown as being placed between the image capturing base 36 and the compression plate 38. The reference numeral 45 represents the chest wall of the subject 32.

The grid 23 is disposed over an upper front surface of the solid-state detector 24 and faces the radiation source 22. The grid 23 serves to remove scattered rays of the radiation X that are generated in the breast 44. The grid 23 comprises an assembly of radiation-permeable members 46 made of aluminum or the like which pass the radiation X therethrough and radiation-impermeable members 48 made of a material including lead or the like. The radiation-permeable members 46 and the radiation-impermeable members 48 extend substantially parallel to each other and also to the chest wall 45 of the subject 32 positioned against the image capturing base 36 along the directions indicated by the arrow A in which the radiation source 22 is angularly movable. The radiation-permeable members 46 and the radiation-impermeable members 48 are disposed alternately in a direction away from the chest wall 45. The radiation-impermeable members 48 are inclined to the horizontal plane of the grid 23 at respective angles θ that are progressively smaller away from the chest wall 45 in alignment with the direction in which the radiation X is applied from the radiation source 22. Therefore, the grid 23 serves as a convergent grid whose focal point is located at the radiation source 22. The grid 23 is reciprocatingly movable in the directions indicated by the arrow C which are perpendicular to the directions in which the radiation-permeable members 46 and the radiation-impermeable members 48 extend.

The solid-state detector 24 comprises a two-dimensional matrix of photoelectric transducers made of amorphous selenium (a-Se) or the like. The solid-state detector 24 converts the radiation X applied to the photoelectric transducers into an electric signal and stores radiation image information represented by the radiation X as electric charge information.

Figure 4:
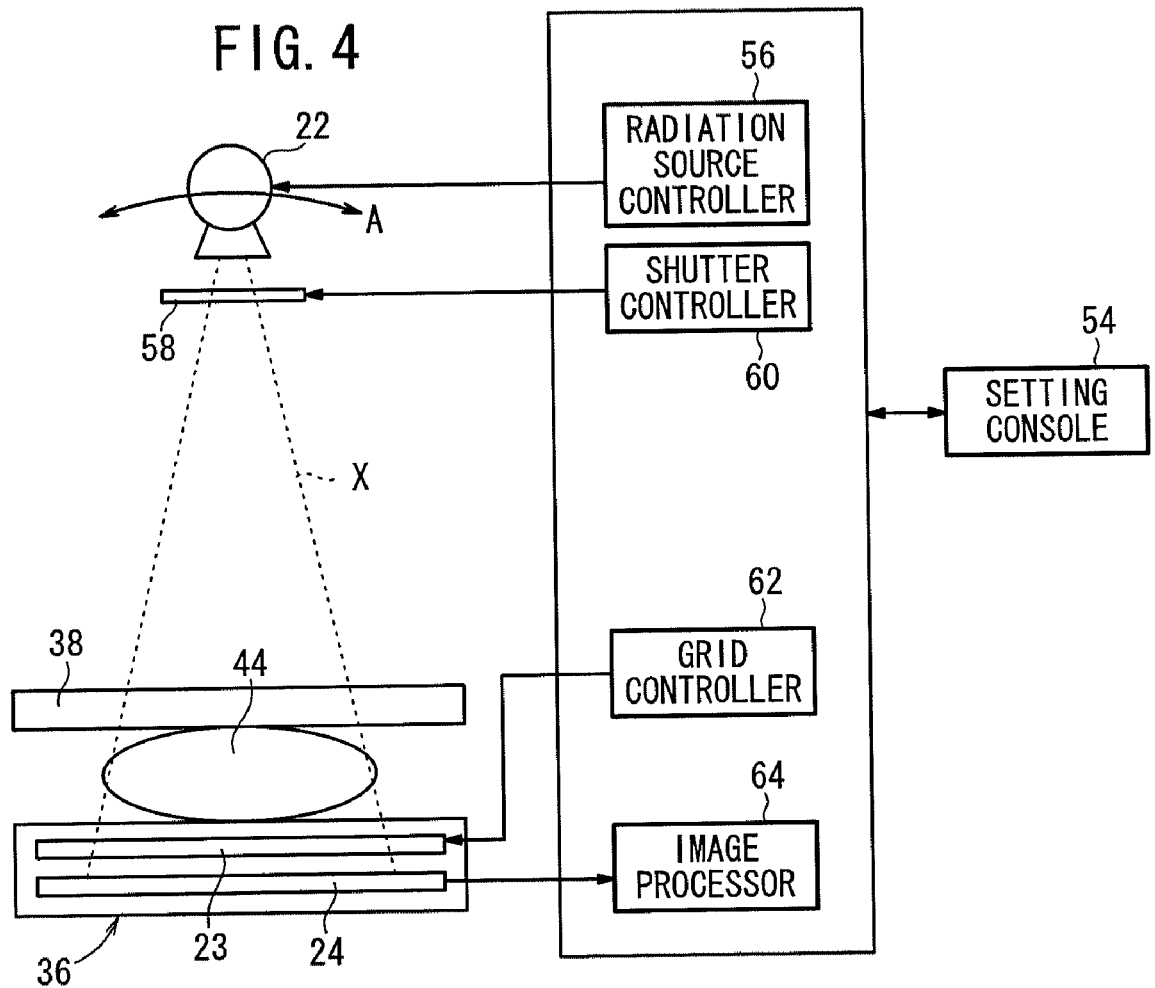
FIG. 4 is a block diagram of a control circuit of the mammographic system according to the embodiment of the present invention.

FIG. 4 shows in block form a control circuit of the mammographic system 20.

As shown in FIG. 4, the mammographic system 20 includes a setting console 54 for setting subject information with respect to the age, sex, body type, subject identification number, etc. of the subject 32, image capturing conditions and an image capturing process for capturing a radiation image, etc., a radiation source controller 56 for controlling the radiation source 22 according to the set image capturing conditions including a tube current, a tube voltage, the types of a target and a filter in the radiation source 22, a calculated irradiation dose of the radiation X, a calculated irradiation time, etc., a shutter controller 60 for actuating a shutter 58 to block the radiation X when the grid 23 is reversed in its movement, a grid controller 62 for controlling the reciprocating movement of the grid 23 in the directions indicated by the arrow C (see FIGS. 2 and 3), and an image processor 64 for processing the radiation image of the breast 44 which is acquired from the solid-state detector 24.

Figure 5:
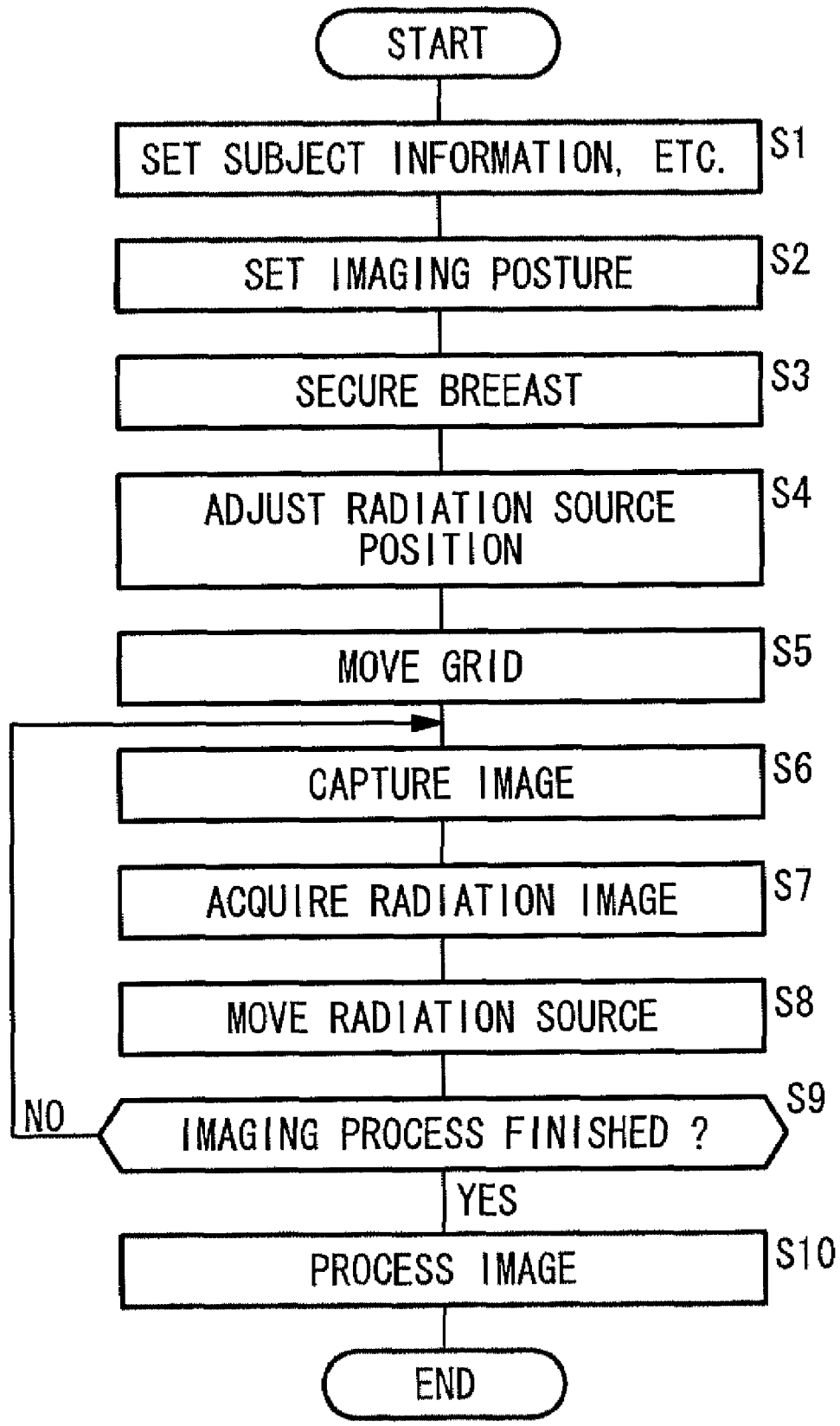
FIG. 5 is a flowchart of an operation sequence of the mammographic system according to the embodiment of the present invention.

The mammographic system 20 according to the present embodiment is basically constructed as described above. Operation of the mammographic system 20 will be described below with reference to a flowchart shown in FIG. 5.

Using the setting console 54 of the mammographic system 20, the operator, who is typically a radiological technician, sets subject information, image capturing conditions, an image capturing process, etc. (step S1). The subject information includes information as to the age, sex, body type, subject identification number, etc. of the subject 32, and can be acquired from an ID card or the like owned by the subject 32. The image capturing conditions include a tube current, a tube voltage, the types of a target and a filter, an irradiation dose of the radiation X, etc. for acquiring a suitable radiation image depending on the breast 44 which is a region to be imaged of the subject 32. The image capturing process represents information including a region to be imaged that is specified by the doctor, an image capturing direction that is specified by the doctor, etc. These items of information can be displayed on the display control panel 40 of the mammographic system 20 for the radiological technician to confirm. If the mammographic system 20 is connected to a network, these items of information can be acquired from a higher-level apparatus through the network.

Then, the radiological technician places the mammographic system 20 into a certain imaging posture according to the specified image capturing process (step S2). For example, the breast 44 may be imaged as a cranio-caudal view (CC) taken from above, a medio-lateral view (ML) taken outwardly from the center of the chest, or a medio-lateral oblique view (MLO) taken from an oblique view. Depending on the information of a selected one of these image capturing directions, the radiological technician turns the arm 30 about the swing shaft 28. In FIG. 1, the mammographic system 20 is set to an imaging posture for taking a cranio-caudal view (CC) of the breast 44.

Then, the radiological technician positions the breast 44 of the subject 32 with respect to the mammographic system 20. For example, the radiological technician places the breast 44 on the image capturing base 36, and thereafter lowers the compression plate 38 toward the image capturing base 36 to hold the breast 44 between the image capturing base 36 and the compression plate 38, as shown in FIG. 2 (step S3).

Figure 6:
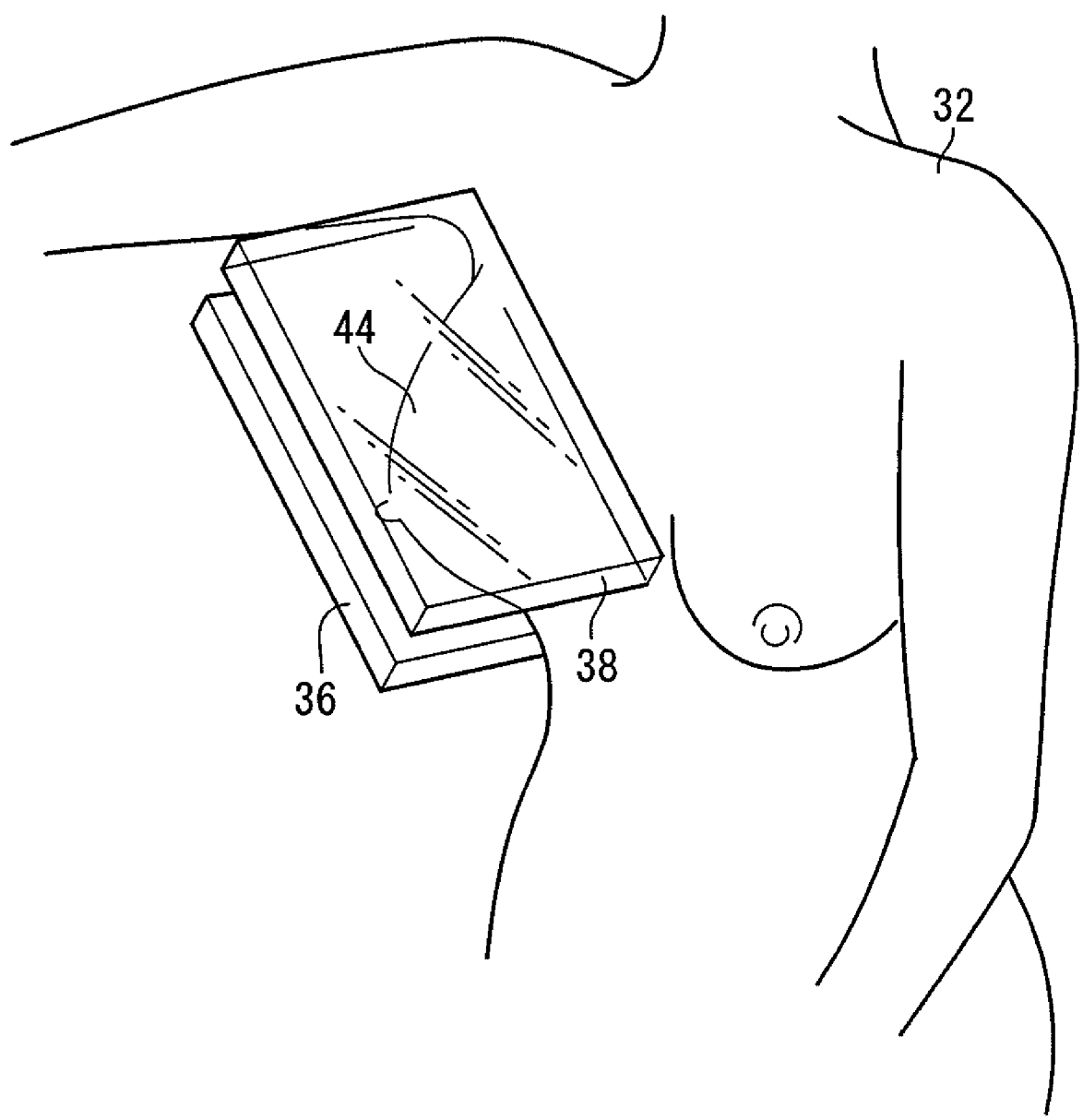
FIG. 6 is a perspective view illustrative of the manner in which a medio-lateral oblique view (MLO) of a breast is captured by the mammographic system according to the embodiment of the present invention.
Figure 7:
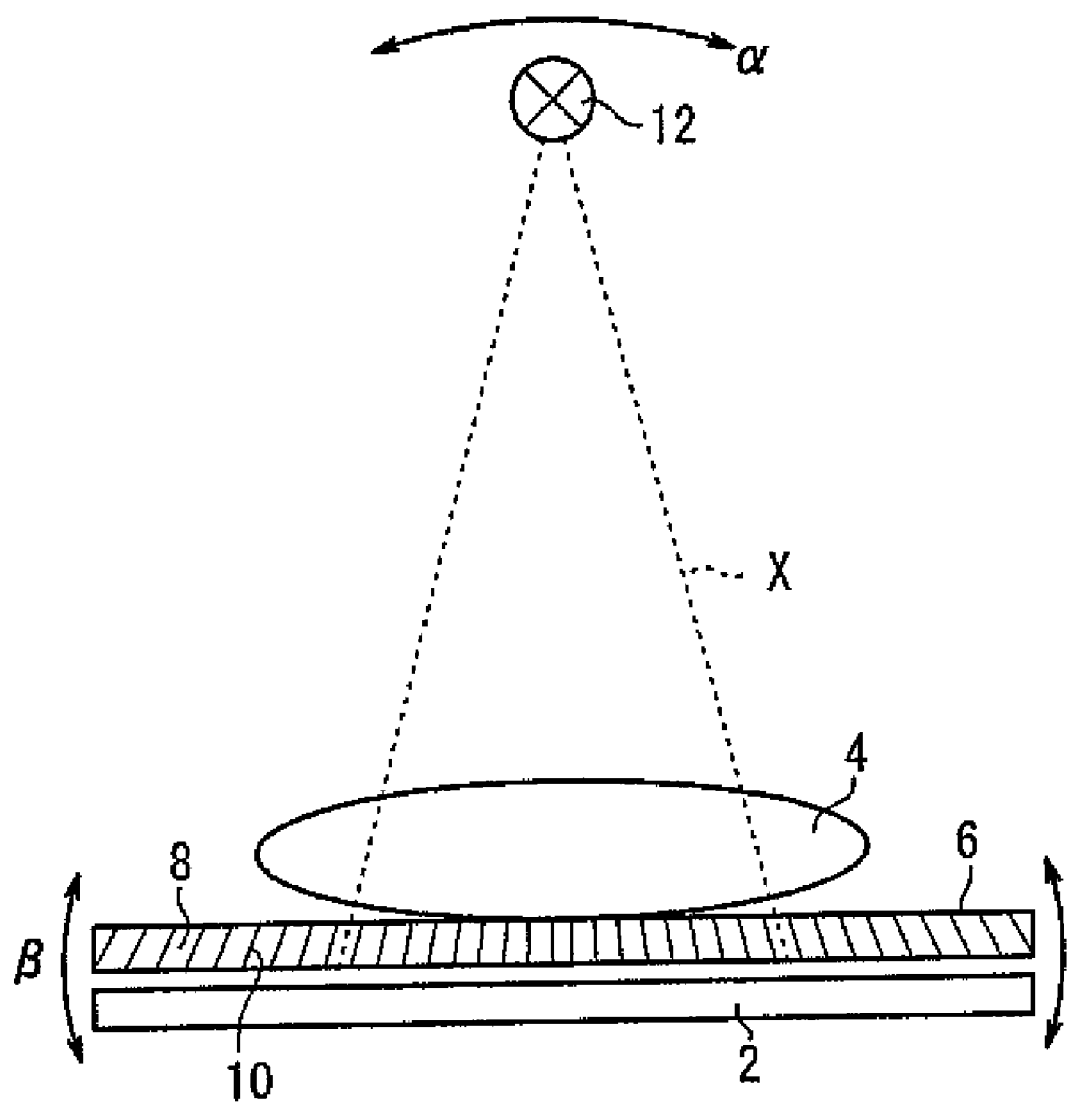
FIG. 7 is a cross-sectional view of a mammographic apparatus of the related art.
Figure 8:
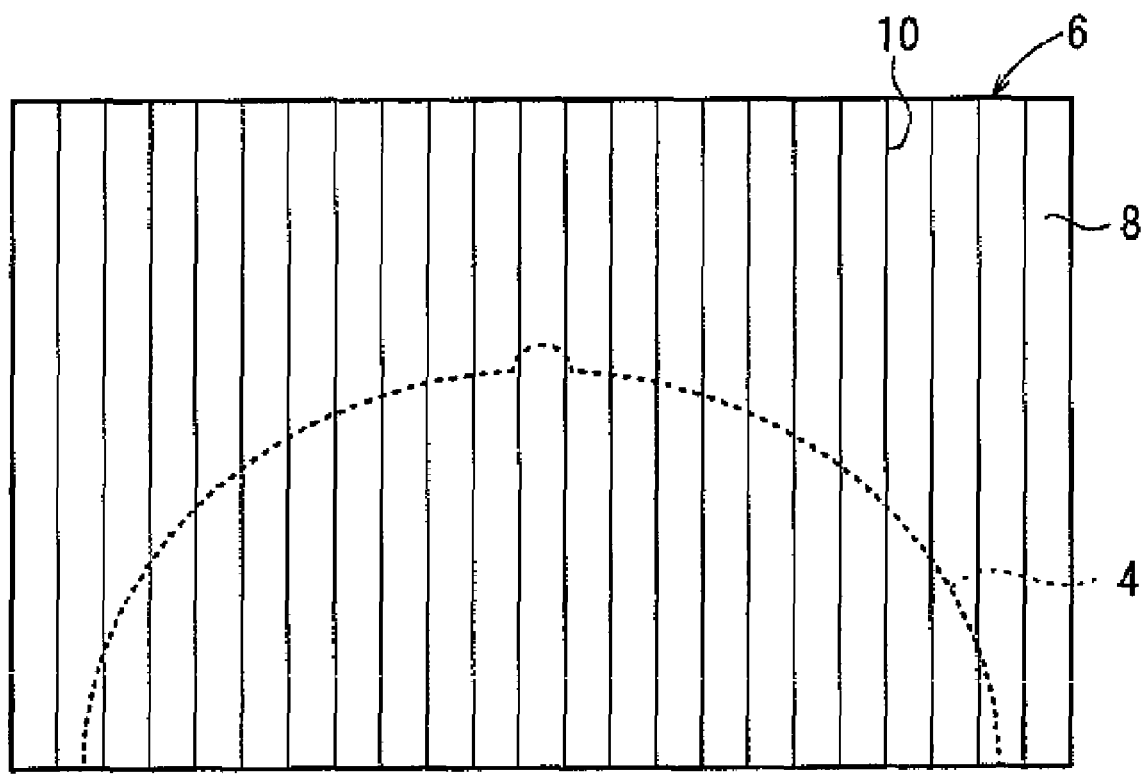
FIG. 8 is a plan view of a grid of the mammographic apparatus of the related art.

FIG. 6 shows the manner in which the mammographic system 20 is set to an imaging posture for taking a medio-lateral oblique view (MLO) of the breast 44, and the breast 44 is fixed between the image capturing base 36 and the compression plate 38 for imaging a medio-lateral oblique view (MLO) thereof. In FIG. 6, since the position of the breast 44 is limited by the upper ends of the image capturing base 36 and the compression plate 38, the breast 44 may possibly be displaced to the lower end of the image capturing base 36, rather than being positioned centrally on the image capturing base 36, depending on the size of the breast 44.

Depending on the position of the breast 44 fixed between image capturing base 36 and the compression plate 38, the radiological technician moves the radiation source housing unit 34 in one of the directions indicated by the arrow A to positionally adjust the radiation source 22 into substantial alignment with the center of the breast 44 (step S4). Since the radiation source 22 moves along the direction in which the radiation-impermeable members 48 extend, the radiation X emitted from the radiation source 22 will not be vignetted by the radiation-impermeable members 48.

Then, the grid controller 62 actuates the grid 23 to reciprocate in the directions indicated by the arrow C (FIGS. 2 and 3) which are perpendicular to the direction in which the radiation-impermeable members 48 extend (step S5). At this time, the grid controller 62 should actuate the grid 23 to reciprocate within a range that is kept in the imaging zone for the breast 44 and in which the radiation X can reach the solid-state detector 24 without being vignetted by the radiation-impermeable members 48.

Then, the radiation source controller 56 controls the tube voltage, the tube current, and the irradiation time of the radiation source 22 according to the image capturing conditions set in step S1 to energize the radiation source 22 for applying the radiation X to the breast 44 to capture a radiation image thereof (step S6).

The radiation X that has passed through the compression plate 38, the breast 44, and the moving grid 23 is applied to the solid-state detector 24, which records a radiation image as electric charge information. The radiation image recorded in the solid-state detector 24 is then acquired by the image processor 64 (step S7).

While the radiation X is being applied to the solid-state detector 24, the grid 23 reciprocates in the directions indicated by the arrow C. At the ends of the stroke of the grid 23, the speed of the grid 23 is nil. If the radiation X is applied to the solid-state detector 24 at the ends of the stroke of the grid 23, shadows of the radiation-impermeable members 48 will be formed in the radiation image.

To avoid the drawback, the shutter controller 60 controls the shutter 58 to block the radiation X emitted from the radiation source 22 when the grid 23 approaches the stroke ends, i.e., nearly when the speed of the grid 23 becomes nil. Consequently, shadows of the radiation-impermeable members 48 are prevented from being formed in the radiation image.

According to a modification, the shutter 58 is dispensed with, and the radiation source controller 56 supplies the radiation source 22 with tube current pulses at a frequency in phase with the frequency of reciprocating movement of the grid 23, for example, such that the radiation source 22 is turned off to interrupt the radiation X nearly when the speed of the grid 23 becomes nil.

When the mammographic system 20 is applied to tomosynthesis, the radiation source 22 is moved through a predetermined angle in one of the directions indicated by the arrow A (step S8). Then, the image capturing cycle from step S6 is repeated until the imaging process is finished (step S9).

Inasmuch as the radiation-impermeable members 48 extend along the directions indicated by the arrow A in which the radiation source 22 moves, the radiation X emitted from the radiation source 22 will not be vignetted by the radiation-impermeable members 48 when the radiation source 22 changes its position. Consequently, the mammographic system 20 is capable of generating a high-quality radiation image free of shadows of the radiation-impermeable members 48.

The radiation image acquired while the radiation source 22 is moving in the directions indicated by the arrow A is processed by the image processor 64 to produce a sectional radiation image or a three-dimensional radiation image (step S10).

The mammographic system 20 may employ a stimulable phosphor panel instead of the solid-state detector 24.

Although certain preferred embodiments of the present invention have been shown and described in detail, it should be understood that various changes and modifications may be made therein without departing from the scope of the appended claims.

What is claimed is:

1. A radiation image capturing apparatus comprising:
   a radiation source for applying a radiation to a breast of a subject;
   a radiation detector for detecting the radiation which has passed through said breast, a side surface of said radiation detector being positioned so as to face a chest wall of the subject; and
   a grid disposed between said breast and said radiation detector for absorbing scattered rays of said radiation, said grid comprising radiation-permeable members extending substantially parallel to said side surface of said radiation detector and radiation-impermeable members extending substantially parallel to said radiation-permeable members, said radiation-permeable members and said radiation-impermeable members being disposed alternately in a direction away from said side surface of said radiation detector.

2. A radiation image capturing apparatus according to claim 1, wherein said radiation-impermeable members are inclined to a plane of said grid at respective angles that are progressively smaller away from the chest wall of said subject, so that said grid serves as a convergent grid whose focal point is located at said radiation source.

3. A radiation image capturing apparatus according to claim 1, further comprising a grid controller for controlling said grid to reciprocate in directions perpendicular to the direction in which said radiation-permeable members and said radiation-impermeable members extend.

4. A radiation image capturing apparatus according to claim 3, further comprising a radiation source controller for controlling said radiation source to inhibit said radiation from being applied to said breast when said grid is reversed in reciprocating movement thereof.

5. A radiation image capturing apparatus according to claim 3, further comprising a shutter for blocking said radiation emitted from said radiation source, said shutter being disposed between said radiation source and said grid, and a shutter controller for controlling said shutter to block said radiation emitted from said radiation source when said grid is reversed in reciprocating movement thereof.

6. A radiation image capturing apparatus according to claim 1, wherein said radiation source is positioned directly above said side surface of said radiation detector, and a radiation direction of said radiation source is directed to said radiation detector.

7. A radiation image capturing apparatus according to claim 1, wherein said radiation source is movable with respect to the subject in a direction in parallel with said side surface.

8. A radiation image capturing apparatus according to claim 1, wherein the radiation is emitted from said radiation source at least at two different angles, and wherein said radiation image capturing apparatus further comprises an image processor for producing a sectional radiation image based on the radiation detected by said radiation detector.

9. A radiation image capturing apparatus comprising:
a radiation source for applying a radiation to a subject, said radiation source being movable with respect to said subject;
a radiation detector for detecting the radiation which has passed through said subject; and
a grid for absorbing scattered rays of said radiation, said grid comprising radiation-permeable members extending substantially parallel to a direction in which said radiation source is movable and radiation-impermeable members extending substantially parallel to said radiation-permeable members, said radiation-permeable members and said radiation-impermeable members being disposed alternately in a direction substantially perpendicularly to said direction in which said radiation source is movable.

10. A radiation image capturing apparatus according to claim 9, wherein said radiation-impermeable members are inclined to a plane of said grid at respective angles that progressively vary along a direction in which said radiation-impermeable members are arrayed, so that said grid serves as a convergent grid whose focal point is located at said radiation source.

11. A radiation image capturing apparatus according to claim 9, further comprising a grid controller for controlling said grid to reciprocate in directions perpendicular to the direction in which said radiation-permeable members and said radiation-impermeable members extend.

12. A radiation image capturing apparatus according to claim 11, further comprising a radiation source controller for controlling said radiation source to inhibit said radiation from being applied to said subject when said grid is reversed in reciprocating movement thereof.

13. A radiation image capturing apparatus according to claim 11, further comprising a shutter for blocking said radiation emitted from said radiation source, said shutter being disposed between said radiation source and said grid, and a shutter controller for controlling said shutter to block said radiation emitted from said radiation source when said grid is reversed in reciprocating movement thereof.

* * * * *